United States Patent
Taylor (10) Patent No.: US 6,562,002 B1
(45) Date of Patent: May 13, 2003

(54) SINGLE DOSE DELIVERY DEVICE

(75) Inventor: Michael A. Taylor, Napa, CA (US)

(73) Assignee: Prismedical Corporation, Napa, CA (US)

(*) Notice: Subject to any disclaimer, the term of this patent is extended or adjusted under 35 U.S.C. 154(b) by 0 days.

(21) Appl. No.: 09/504,179

(22) Filed: Feb. 15, 2000

Related U.S. Application Data (60) Provisional application No. 60/120,418, filed on Feb. 16, 1999.

(51) Int. Cl.⁷ .............................................. A61M 37/00
(52) U.S. Cl. ...................................................... 604/82
(58) Field of Search ........................... 604/82–92, 187, 604/199, 235, 200

(56) References Cited

U.S. PATENT DOCUMENTS

| | | | |
|---|---|---|---|
| 5,222,948 A | | 6/1993 | Austin et al. |
| 5,281,198 A | | 1/1994 | Haber et al. |
| 5,308,348 A | | 5/1994 | Balaban et al. |
| 5,336,180 A | * | 8/1994 | Kriesel et al. ............... 604/82 |
| 5,360,410 A | | 11/1994 | Wacks |
| 5,476,449 A | | 12/1995 | Richmond |
| 5,569,191 A | * | 10/1996 | Meyer ...................... 604/82 |
| 5,685,846 A | | 11/1997 | Michaels, Jr. |
| 5,722,955 A | | 3/1998 | Racz |
| 5,725,777 A | | 3/1998 | Taylor |
| 5,807,323 A | | 9/1998 | Kriesel et al. |
| 6,387,074 B1 | * | 5/2002 | Horppu et al. ............... 604/89 |

* cited by examiner

*Primary Examiner*—Brian L. Casler
*Assistant Examiner*—Ann Y. Lam
(74) *Attorney, Agent, or Firm*—Knobbe, Martens, Olson & Bear, LLP (57) ABSTRACT

A microinjection system comprises a device for housing dried forms of medical reagents, such as vaccines, hormones, etc. in single doses. Within a single chamber, a dry reagent bed is provided adjacent a compression component that keeps the bed compacted. In operation, diluent flows through the chamber to carry the reagent out of the chamber in fluid form. In the illustrated embodiments, the fluid carrying reagent is directly delivered from the chamber via a needle. Integral or connectable diluent delivery devices are disclosed for providing an appropriate volume of diluent to the reagent chamber. Unstable formulations of drugs, for example, can be safely stored in dry form. When injection is needed, the drug can be delivered almost instantly in fluid form simply by releasing diluent through the chamber, where the reagent bed is dissolved or suspended while the remaining reagent is continually compacted. The resultant fluid contains a single dose of the reagent and is delivered directly to a patient, desirably without measurement of the fluid form.

31 Claims, 5 Drawing Sheets

SINGLE DOSE DELIVERY DEVICE

REFERENCE TO RELATED APPLICATION

This application claims the priority benefit under 35 U.S.C. §119(e) from provisional Application No. 60/120,418, filed Feb. 16, 1999.

FIELD OF THE INVENTION

The present invention relates generally to the administration of drugs, and more particularly to the dissolution and admininistration of drugs from dry formulations.

BACKGROUND OF THE INVENTION

Injection of micro-quantities of soluble drug is used extensively throughout the world for a wide range of drugs, reagents and biological substances. Many of these reagents are unstable in their liquid form under various conditions. An effective method for maintaining these unstable drugs in a stable condition is to keep the reagent as a dry formulation.

Current methods for administering dry formulations into patients involves adding a liquid diluent into a vial containing the dry reagent to be administered. The dry reagent is allowed to dissolve within the vial. This frequently requires some minimal agitation. Too much agitation can result in foaming of the reagent and preventing recovery of the appropriate amount of drug to administer to the patient. Following dissolution of the reagent, the reagent solution is withdrawn from the vial in a syringe. This charged syringe is then used to inject the patient. To assure that the proper amount of reagent is delivered, it is desirable to be able to view the reagent as it is administered.

One type of device for administering liquid drugs to a patient is the single-use syringe design described in U.S. Pat. No. 5,222,948. This device provides a means of a single use injection with a one way valve system that incorporates a needle and a separate solution chamber. The reagent to be delivered is contained as a solution within the solution chamber. For many applications, the reagent should remain stable in solution over relatively long periods of storage and/or transportation. Unfortunately, many reagents that could be delivered from this device are not stable in solution. Such reagents are, as a rule, considerably more stable as a dry form, i.e., powder or lyophilized.

SUMMARY OF THE INVENTION

The description herein describes systems, devices and methods for providing fluid forms of bioactive reagent from dry forms of the reagent.

In accordance with one aspect of the invention, a system is provided for delivering single dose units of medical reagents in fluid form. The system includes a chamber that houses a dry reagent bed having a mass of no more than about 1.0 g. A compression component in the chamber exerts pressure upon the reagent bed. A delivery mechanism is integrally connected downstream of the chamber for delivering the reagent in a liquid.

In the illustrated embodiments, the system also includes an upstream source of diluent for reconstituting the dry reagent in fluid form within the chamber, in route to the delivery mechanism. The preferred delivery mechanism is an injection needle.

In accordance with another aspect of the invention, a method is provided for preparing and delivering a defined drug dose. The method includes converting a dry reagent into a fluid form by flowing a diluent along a laminar flow path through a chamber that houses the dry reagent. The fluid is then delivered from the chamber directly into a delivery mechanism in fluid communication with a drug recipient.

BRIEF DESCRIPTION OF THE DRAWINGS

These and other aspects of the invention will be apparent to the skilled artisan from the description below and from the drawings, which are meant to illustrated and not to limit the invention, and in which.

DETAILED DESCRIPTION OF THE PREFERRED EMBODIMENTS

This invention relates to improvements in preparing and administering defined doses of drugs. The invention disclosed herein also relates to a means of maintaining potentially unstable, injectable reagents in a stable form, as dry formulations, until administration to the patient. The patient can be human or can be another animal.

While the embodiments of the invention are described in the context of dry reagent reconstitution, the skilled artisan will find application for the principles disclosed herein in a variety of contexts, particularly where dissolution of reagents that are unstable in solution is desired.

As described in detail below, the preferred embodiments provide a drug delivery system comprising a microinjector device for reconstituting and administering a reagent of choice. The microinjector is adapted to be mechanically associated with a diluent source, where the diluent is used to reconstitute the dry reagent. As discussed below, the diluent may be supplied by a number of devices, such as a syringe.

Diluents for use with the invention dissolve or suspend the reagent of choice within the microinjector. The dry or dried reagent resides as a reagent bed within the microinjector and is confined in a reagent chamber held between one or more porous compression components and/or a wall of the housing of the microinjector device. The compression component, discussed in detail below, provides the means by which the reagent is evenly and consistently dissolved by the diluent.

The microinjector disclosed herein can be used in a one-time use fashion or it can be constructed for multiple uses. A reusable microinjector would be constructed in such a manner as to permit refilling of the reagent volume used within the device, as well as permitting the recompression of the compressor component; both features are discussed below. Concerning design specifications, the microinjector device contemplated herein can be constructed in various sizes for use with various quantities of dry reagents.

One embodiment of the invention includes a suitable diluent, a reagent contained within the device that is to be administered to a subject in need thereof and a microinjection device for preparing and administering the reagent. As described herein a suitable diluent is contemplated as including any liquid suitable for carrying and delivering dry drugs or other reagents. Examples of such diluents include saline and sterile water. The diluent can also contribute medically active agents to the delivered fluid, as will be appreciated from Example I detailed below. Separation of bioactive ingredients into the diluent and the dry reagent bed can advantageously avoid reaction between such agents by avoiding long storage together in solution form.

The range of dried drugs and reagents usable with the invention disclosed herein is contemplated to encompass any of a number of compounds, particularly those designed for medical applications. The illustrated microinjection device employs a bioactive reagent that can be substantially dried and subsequently reconstituted, dissolved, or suspended in water. The amount of the dry reagent will vary according to that agent and the quantity of the compound, or compounds that is effective for providing a single dose of the reagent. "Single dose," as used herein, refers to an amount of the reagent desirable for direct delivery to a patient, without further measurement prior to delivery. "Direct delivery" may be directly into a patient via an injection needle (e.g., intravenously or intramuscularly), or by way of an IV drip line. In either case, the dissolved or, reconstituted reagent is administered to the patient without further measurement.

The reagent to be contained can be soluble or insoluble. The devices described herein dissolve soluble reagents and deliver the reagent in a solution. The reagents. could consist of powders, freeze-dried agents, crystals or granules. Insoluble agents are suspended or otherwise liberated from the confined dry form and delivered as a suspension or slurry upon hydration with the diluent fluid. The amount of dry reagent varies widely with the reagent and diluent of choice, but is preferably less than about 1.0 g, desirably ranging from about 10 μg to 500 mg, more preferably 1 mg to 100 mg, and most preferably from about 1 mg to 25 mg. The amount of diluent employed will, of course, generally vary with the desired dosage of reagent and vice versa.

Examples of reagents contemplated for use with the invention include antivenoms, antibiotics, anti-inflammatories, coagulation agents, vaccines, hormones (e.g., synthetic insulin), biotechnology derived agents (e.g., lyophilized proteins), and the like. Particular examples of medical compounds that are or could be produced in dry formulations for reconstitution in the microinjector immediately prior to administration are listed in Table I below:

TABLE I

| Reagent Class | Generic Name(s) | Trade Name | Manufacturer |
|---|---|---|---|
| Vaccine | Measles, Mumps, Rubella | MMR II | Merck of West Point, PA |
| Vaccine | Rabies | Imovax | Pasteur Merieux Connaught of Swiftwater, PA |
| Hormones | Human Growth Hormone | Geref | Serono of Norwell, MA |
| Immune Modulators | Interferon | Intron A | Schering of Kenilworth, NJ |
| Antivenins | Antitoxins | Antivenin | Merck of West Point, PA |
| Antibiotics | Cephalosporins: Cefazolin | Anacef | SmithKline Beecham of Pittsburgh, PA |
| Antivirals | | Retrovir | Glaxo Wellcome of Research Triangle Park, NC |
| Antidiabetic | Insulins, natural and synthetic | Actimmune | InterMune of Palo Alto, CA |
| Antineoplastics | Nitrogen Mustards | Cytoxan | Bristol-Myers Squibb of New York, NY |
| Toxoids | Tetnus Toxid | Infanrix | SmithKline Beecham of Pittsburgh, PA |

The reagents may be prepared using any one of a number of water removing technologies that are well known in the art. For example, the drugs to be administered can be lyophilized, freeze-dried, crystallized, or granulized.

The reagent may be incorporated into the structure of the microinjector through. a variety of means. In one embodiment, a dry reagent of choice is added to the reagent chamber of the microinjector and then sealed therein. In another embodiment, the drug to be administered is dried inside of the injector body. This design provides a means of incorporating lyophilization of reagent within the microinjector during the assembly process. Prior to sealing the top in place, the housing is placed into the bottom cover The reagent is placed in the housing as a solution. The entire subassembly is frozen and placed into a lyophilization system to freeze-dry the reagent inside the microinjector. After the reagent is freeze-dried, the compression component is seated and compressed within the housing and the top is then sealed in place. Advantageously, the reagent remains sealed in a stable, dry form until the moment of administration.

The reagent is preferably deliverable to a patient via a diluent. Although the following description discusses dissolving reagents, it should be understood that any system for mixing a dried reagent with a diluent to form a deliverable liquid is contemplated. For example, microinjection systems that introduce suspensions, slurries or other mixtures of liquid and dried reagents into a patient are contemplated.

With respect to the volume of diluent contained in the diluent-providing device, the volume should be sufficient to dissolve the entire quantity of reagent present in a particular microinjection device. Preferably, the volume of diluent ranges from 0.1 mL to 100 mL of fluid. More preferably, the volume of diluent ranges from 0.1 mL to 10 mL of fluid. Most preferably, the volume of fluid contained within the diluent is 0.1 mL to 1 mL.

Microinjector Device

Figure 1:
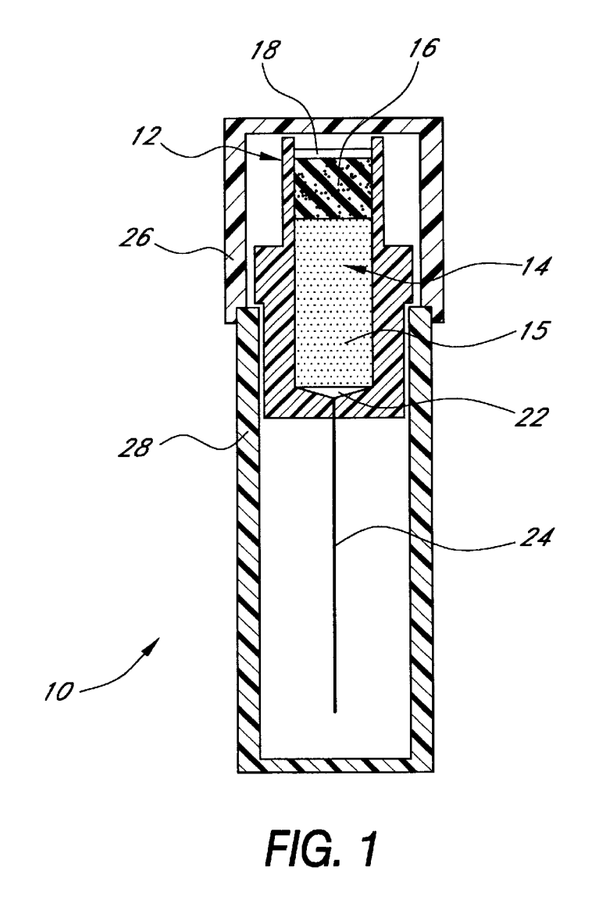
FIG. 1 is a schematic cross-section of a microinjector, constructed in accordance with a preferred embodiment of the present invention, with a compression component compacting a drug bed and having top and base covers in place.
Figure 2:
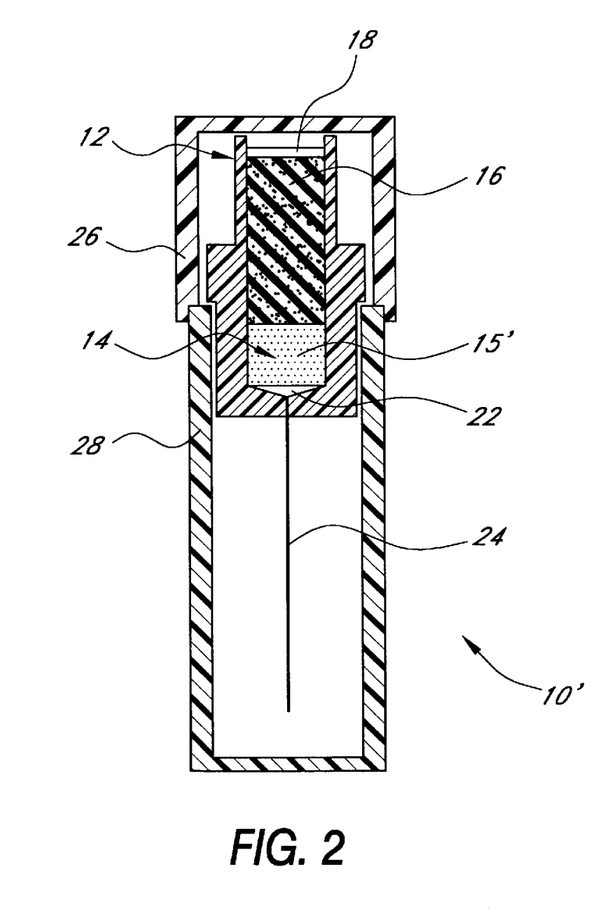
FIG. 2. shows a microinjector similar to FIG. 1 with the compression component expanded to compact a smaller drug bed, relative to FIG. 1, and the top and base covers in place.

With reference to FIGS. 1 and 2, one embodiment of the invention includes a microinjection device 10 comprising a single-use, clear walled housing 12 that defines a reagent chamber 14, shaped and sized to house a reagent bed 15 and a porous compression component 16. The total volume of the reagent chamber, housing both the reagent bed 15 and the compression component 16, is preferably between about 0.1 mL and 10 mL, more preferably between about 0.15 mL and 2 mL. The housing 12 may be constructed of any suitable material that provides a substantially rigid structure and is preferably sufficiently transparent to permit the visualization of fluid and dissolution of the reagent bed 15 within the device during or before operation. Example of suitable materials includes glass, polypropylene, polystyrene and the like.

The compression component 16 occupies a range of conformations extending from a compressed conformation to a decompressed conformation. When axially compressed, as shown in FIG. 1, the compression component 16 is biased to elastically expand and exert pressure in the axial direction, tending to compress the reagent bed 15 and occupy any volume in the chamber 14 not occupied by the reagent bed 15. Thus, as shown in FIG. 2, the same compression component 16 can be employed in a different microinjector 10' with a differently sized reagent bed 15', and yet still be effective in exerting pressure thereupon.

The compression component 16 can be any type of open cell foam with elasticity. For example, polyurethane foam, polyethylene foam or polypropylene foam are all contemplated for use with the disclosed invention. Either the foam itself or a frit, interposed between the elastic foam and the reagent bed, has a pore size that is smaller than the smallest particle in the reagent bed. Other mechanisms that function in a manner similar to that of a foam compression component are also contemplated. For example, plastic or metal springs can also be used in conjunction with a frit. Reference is made to the compression components and operation in compacting reagent beds in U.S. Pat. No. 5,725,777, issued Mar. 10, 1998, the disclosure of which is incorporated herein by reference.

The preferred location of the compression component 16 is influenced by the solubility of the reagent. A single compression component 16 is preferably placed upstream insoluble agents, as shown. In other arrangements, two compression components can be employed, e.g., upstream and downstream of the bed. A downstream compression component can also serve as a hydrophilic or microporous plug for creating backpressure to overcome during operation, inhibiting premature flow and ensuring complete wetting of the reagent bed 15.

The housing 12 includes an upper seal 18, which closes off the chamber 14 during assembly. The outlet of the reagent chamber 14 forms an inverted cone 22 with the apex terminating in a delivery mechanism that introduces the reagent to a patient. Preferably, this mechanism comprises a terminal needle 24 for injection into the patient. However, other types of devices, such as Luer connectors into drug delivery lines (e.g., intravenous drip), or any other connector that allows introduction of the liquefied reagent into a patient, can be substituted in other arrangements. The illustrated needle 24 is of sufficiently small bore to prevent passive fluid passage without application of external pressure.

Alternatively or in addition to the constriction of the needle 24, a porous plug or frit can be inserted in the downstream end or terminus 22 of the reagent chamber 14. The porosity of such a plug is preferably sufficiently small to prevent passive fluid passage to the reagent chamber 14 and ensure complete wetting of the reagent bed 15. The component 16 can also be composed of hydrophobic materials for the same purpose. As noted above, a downstream compression component can be configured to serve as the downstream plug. The needle constriction and/or plug also serve to prevent escape of reagent particles from the reagent bed 15 prior to operation of the device 10. Furthermore, sufficient backpressure is generated to ensure dissolution of the reagent prior to delivery through the needle 24.

The microinjector 10 is enclosed within two covers 26, 28. A top cover 26 covers and protects the upper end of the housing 12. A base cover 28 covers the lower end of the housing 12 and the exposed needle 24. The illustrated covers 26, 28 are held in place by a snap fit to the housing 12. For example, an indented groove (not shown) on the housing 12 is sized and shaped to mate with a convex ridge on the base cover 28. Similar grooves and convex ridges on the base cover 28 and the top cover 26, respectively, provide a snap fit to hold the two covers 26, 28 together.

Diluent Delivery Device

Figure 3:
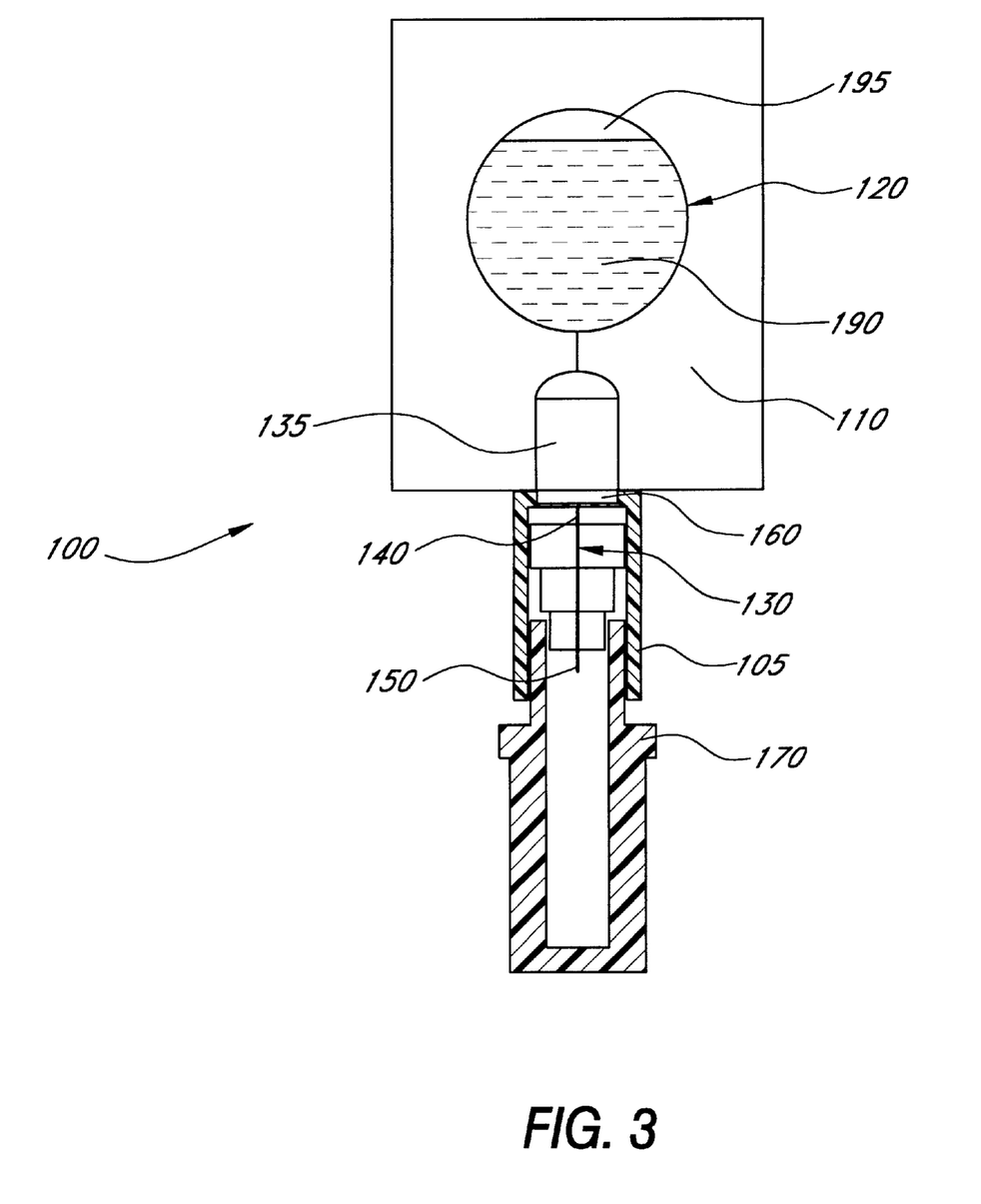
FIG. 3 is a schematic cross-section of a diluent device, constructed in accordance with the preferred embodiment.

Another aspect of the invention comprises provision of a diluent delivery device 100, shown in FIG. 3. The apparatus 100 is configured to deliver a suitable sterile diluent with the microinjector device of 10 of FIG. 1, as further described herein below. The diluent device 100 is therefore provided with a downstream diluent collar 105 capable of mating with other medical devices in general, and in particular with the microinjector device 10 of FIG. 1.

The illustrated diluent device 100 comprises a diluent housing 110, including a diluent chamber 120 and a connecting needle 130, extending from a proximate needle end 140 to a distal needle end 150. The device shown in FIG. 3 also contain a channel 135 providing a means through which diluent may pass. Between the diluent chamber 120 and the needle 130 is a diluent chamber seal 160. The base of the device 100 is covered by a diluent device cover 170. This cover forms a seal and protects the needle 130 by fitting within the diluent device collar 105.

The diluent chamber 120 preferably comprises a flexible plastic tab that can be compressed to expel fluid through the channel 135. The diluent chamber 120 contains a suitable diluent 190 and most preferably a gas 195. The gas 195, if properly oriented during operation, allows complete expulsion of the diluent 190. Alternatively, a precise amount of excess diluent can be employed, such that only the excess diluent is left within the device after injection. In the illustrated embodiment, the diluent 190 comprises distilled, deionized or otherwise sterilized water or saline. As set forth in Example I below, the diluent 190 can also contribute bioactive components to the delivered fluid. Desirably, the small needle aperture prevents passage of the diluent 190 through the channel 135 in the absence of positive pressure on the exterior of the chamber 120, even after the seal 160 is pierced. The chamber walls are preferably transparent enough to view the presence or absence of diluent in the, chamber 120.

In other arrangements, the diluent chamber can be provided with other mechanisms to provide fluid flow. For example, a spring-loaded mechanism can be triggered or released to allow the spring to thereafter automatically squeeze diluent out of the device. In this manner, the amount of diluent released during operation does not rely upon the finger pressure and length of time an individual exerts pressure upon the diluent housing. Rather, a defined pressure is exerted by the spring-loaded mechanism to assure complete expulsion of the diluent at a predictable and repeatable rate of flow.

Assembly and Operation

In operation, the microinjector 10 is first placed in fluid communication with a diluent source. In the preferred embodiment of FIGS. 4–6, the diluent delivery device 100 of FIG. 3 is connected in series with the microinjector 10 of FIG. 1 to produce a microinjector system 198.

Figure 4:
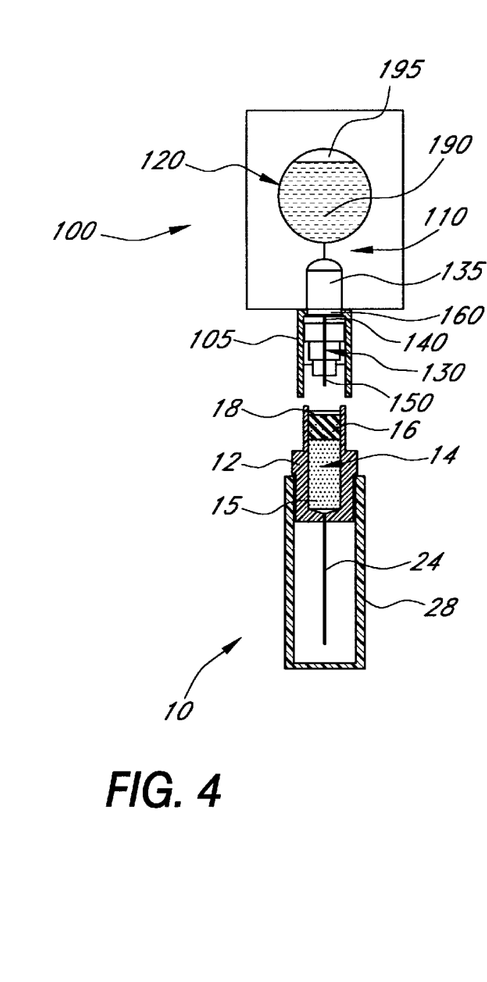
FIG. 4 shows the microinjector of FIG. 1, with the top cover removed, aligned beneath the diluent device of FIG. 3, also having its cover removed.

With reference to FIG. 4, the cover 170 (FIG. 3) of the diluent device 100 is removed from the diluent device collar 105. The top cover 26 (FIG. 1) of the microinjection device 10 is also removed from the embodiments shown in FIGS. 4–6. The microinjector 10 is inserted into the diluent housing collar 105, as shown. With the microinjector base cover 28 in place, the microinjector 10 is pushed into the diluent housing collar 105 until the proximal needle end 140 within the collar 105 perforates the junction 160 between the housing collar 105 and the diluent channel 135. An open connection is thus created between the diluent 190 in the diluent chamber 120 and the diluent device needle 130.

At the same time, the distal needle end 150 perforates the microinjector cap or seal 18. This creates a connection between the needle 130 and the reagent chamber 14, and thereby between the diluent chamber 120 and the reagent chamber 14 via the needle 130. With this connection created, the housing, base cover 28 is removed, exposing the injection needle 24, and the combined system is used to inject the patient.

Figure 6:
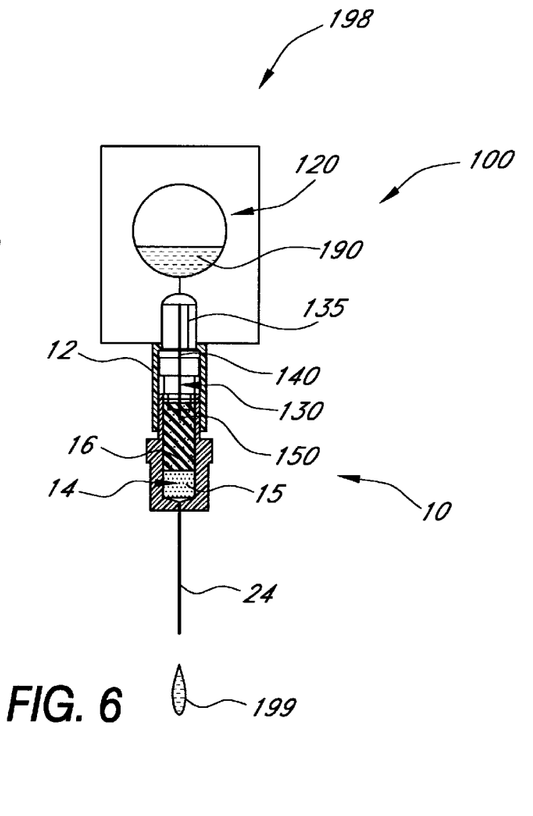
FIG. 6 illustrates the microinjector and diluent device of FIG. 5 expelling solution as the diluent flows and the compression component expands.

As shown in FIG. 6, reagent solution 199 is provided through the injection needle 24 by squeezing the diluent chamber 120, forcing the diluent 190 out of the diluent chamber 120, through the needle 130 and into the reagent chamber 14. One feature of the compression component 16 is that, when, in the compressed conformation, the residual porosity of the component allows diluent to flow through the component 16 to the reagent bed 15. Passage of the diluent 190 through the reagent bed 15 results in dissolution of the reagent. The fluid flow path of the diluent through the compression component is such that it contacts the plane of the reagent bed 15 in a substantially equal manner. The fluid flow through the compression component 16 and the manner in which the diluent contacts the reagent bed 15 contributes to the effectiveness of the dry reagent's reconstitution (e.g., dissolution) into the flowing diluent.

As diluent 190 flows through the reagent chamber 14, preferably along a laminar flow path, the dry reagent bed 15 contained therein is reconstituted in an even and consistent manner. The compression component 16 exerts an axial pressure on the dry reagent bed 15 contained within the reagent chamber 14. The compressed component 16 serves to distribute the diluent in such a way as to cause the even dissolution of the reagent by the diluent. As the reagent dissolves, the compression component 16 expands (FIG. 6) to replace lost reagent and fill the reagent chamber 14. During the dissolution process, no voids or channels are formed in the reagent bed as the expanding compression component 16 continually compacts the reagent bed 15. The expansion of the compression component 16 continues until all of the reagent bed 15 is dissolved and the reagent chamber 14 is filled with the expanded compression component 16. Accordingly, consistent pressure from the compression component results in the even and complete dissolution of the dry reagent, assuring delivery of the correct reagent dosage.

External pressure is maintained on the diluent chamber 120 of the microinjector system 198 until all the diluent is expelled from the preferred diluent device 100, the diluent housing needle 130, the microinjector reagent chamber 14 and the microinjector needle 24. The clear housing 12 enables visualization of the dissolution of the reagent, as well as the expulsion of the reagent solution 199 from the reagent chamber 14 and into the patient.

The following examples are provided as a particular embodiment of the invention. The examples are meant to illustrate and not limit the scope of the invention in any manner.

EXAMPLE I

In one example, the microinjector system delivers an intramuscular injection of a combination of reagents. In particular, an anti-cholinergic agent (atropine) is delivered along with an anti-nerve agent (HI-6). This combination of agents is used as an antidote for chemical warfare agents that attack the nervous system.

For an exemplary dosage, the microinjection system comprises a stored diluent that includes 2 mg of atropine in 2.5 mL of sterile water. The dry reagent bed comprises 500 mg of HI-6. As the diluent passes through the bed of HI-6, the dry reagent is dissolved and delivered to the patient as a solution, including active ingredients from each of the diluent and the dry reagent bed. With the illustrated device, the dissolution and deliver is conducted within roughly 5 seconds. Atropine and HI-6 are available from Sigma-Aldrich Corp. of St. Louis, Mo. and Phoenix Chemical Laboratory, Inc. of Chicago, Ill., respectively.

EXAMPLE 2

The reagent chamber is loaded with a quantity of epinephrine efficacious in the treatment of an allergic reaction to bee stings. An adult dose is about 0.3 mg. The reagent chamber is loaded with epinephrine hydrochloride, commercially available from Sigma-Aldrich of St. Louis, Mo. Additionally, the reagent bed comprises salts for better physiologic composition of the injected drug. In particular, the reagent bed can comprise about 0.31 mg of calcium chloride, 0.30 mg of potassium chloride, and 8.6 mg of sodium chloride. The compression component is in physical contact with the reagent in the chamber. The diluent comprises a fluid capable of rapidly dissolving crystallized epinephrine, particularly about 2.5 mL of sterile water for injection. The above quantity of reagents is assembled in the structure as recited and will produce approximately 2.75 mL of epinephrine diluted in Ringer's solution, suitable for direct injection into a patient.

Alternative Assemblies

Figure 5:
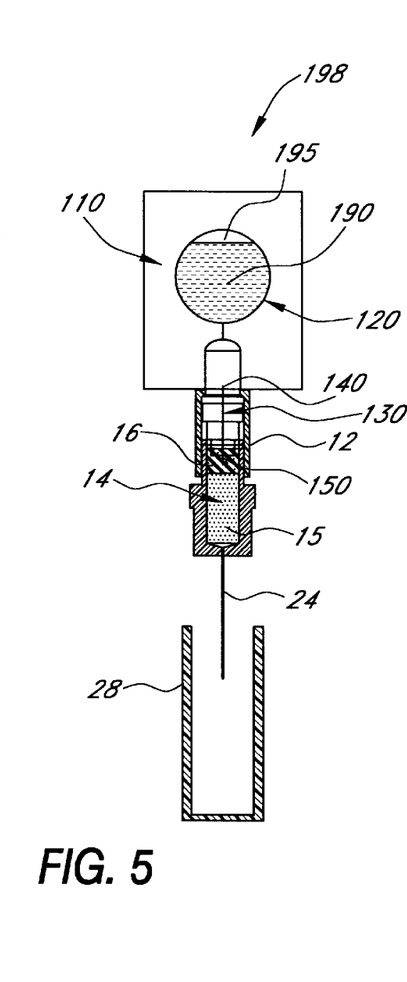
FIG. 5 is a schematic cross-section of the microinjector connected to the diluent device of FIG. 4, with the microinjector base cover removed.

The microinjector 10 can be employed in series with a separate diluent delivery device 100, as described with respect to FIGS. 4–6. The skilled artisan will readily appreciate, however, that the microinjector 10 can also be employed with other diluent sources for dissolving or otherwise mixing the reagent bed for delivery.

Figure 7:
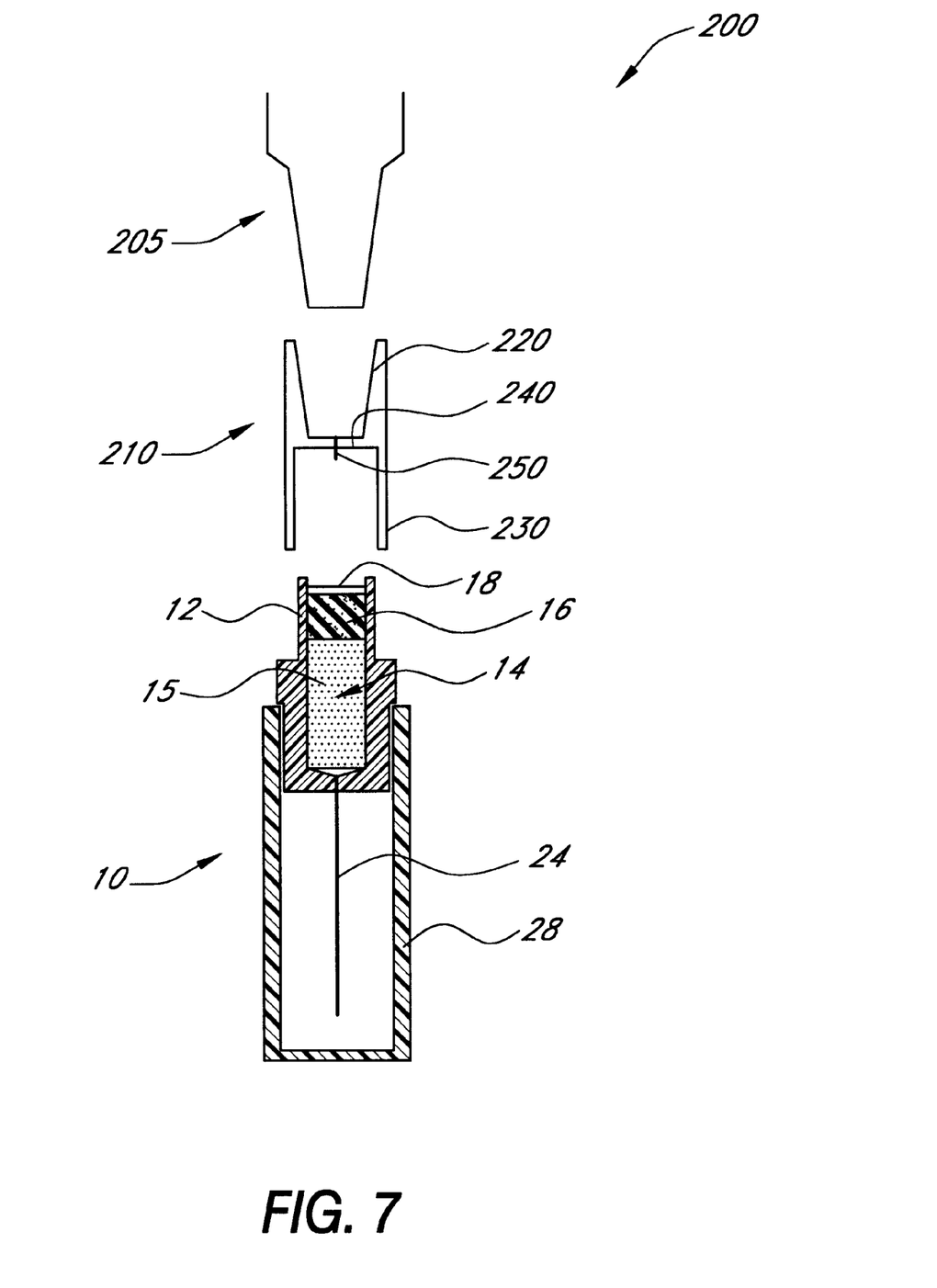
FIG. 7 is a schematic cross-section of a microinjector, constructed in accordance with another embodiment of the invention, including an adaptor for Luer attachments.

With reference to FIG. 7, for example, a microinjector, system 200 is provided for use with a standard Luer-type fitting 205. The embodiment is illustrated with the microinjector 10 of FIG. 1. A simple Luer adaptor 210 adapts the diluent source (having the Luer fitting 205 at a downstream end) for fluid communication with the upstream end of the microinjector 10. An exemplary diluent delivery device for use with the illustrated embodiment comprises the one-time use syringe described in U.S. Pat. No. 5,222,948, the disclosure of which is incorporated herein by reference.

The Luer fitting 205 inserts into the Luer adaptor 210. The adaptor 210 includes a standard Luer fitting receiver 220 at an upstream end. The downstream end comprises a collar 230 with a groove-and-ridge snap-to-fit design configured to attach to the exterior of the housing 12 of the microinjector 10. A bridge 240 between the receiver 220 and the collar 230 includes a needle 250, establishing fluid communication between the receiver 220 and the collar 230.

In operation, the Luer adaptor 210 is connected to the syringe (e.g., of the '948 patent) in a similar manner as the connection of the microinjector 10 to the diluent device 100 of FIGS. 4–6. This embodiment can also be used with a syringe using the Luer.attachment. With the base cover 28 in place over the microinjector 10 and its needle 24, the microinjector 10 is inserted into the Luer adaptor 210 via the collar 230. The Luer fitting 205 of the diluent delivery device (e.g., syringe) is inserted into the receiver 220 of the adaptor 210. Pressing all three components together seats the syringe into the adaptor 210. The adaptor needle 250 perforates the seal 18 of the microinjector 10 and creates a connection created between the fluid within the syringe and the terminal needle 24 of the microinjector 10. The base cover 28 can then be removed, the needle 24 inserted into the patient or IV line, and, diluent flows through the system to carry reagent out of the needle 24.

Figure 8:
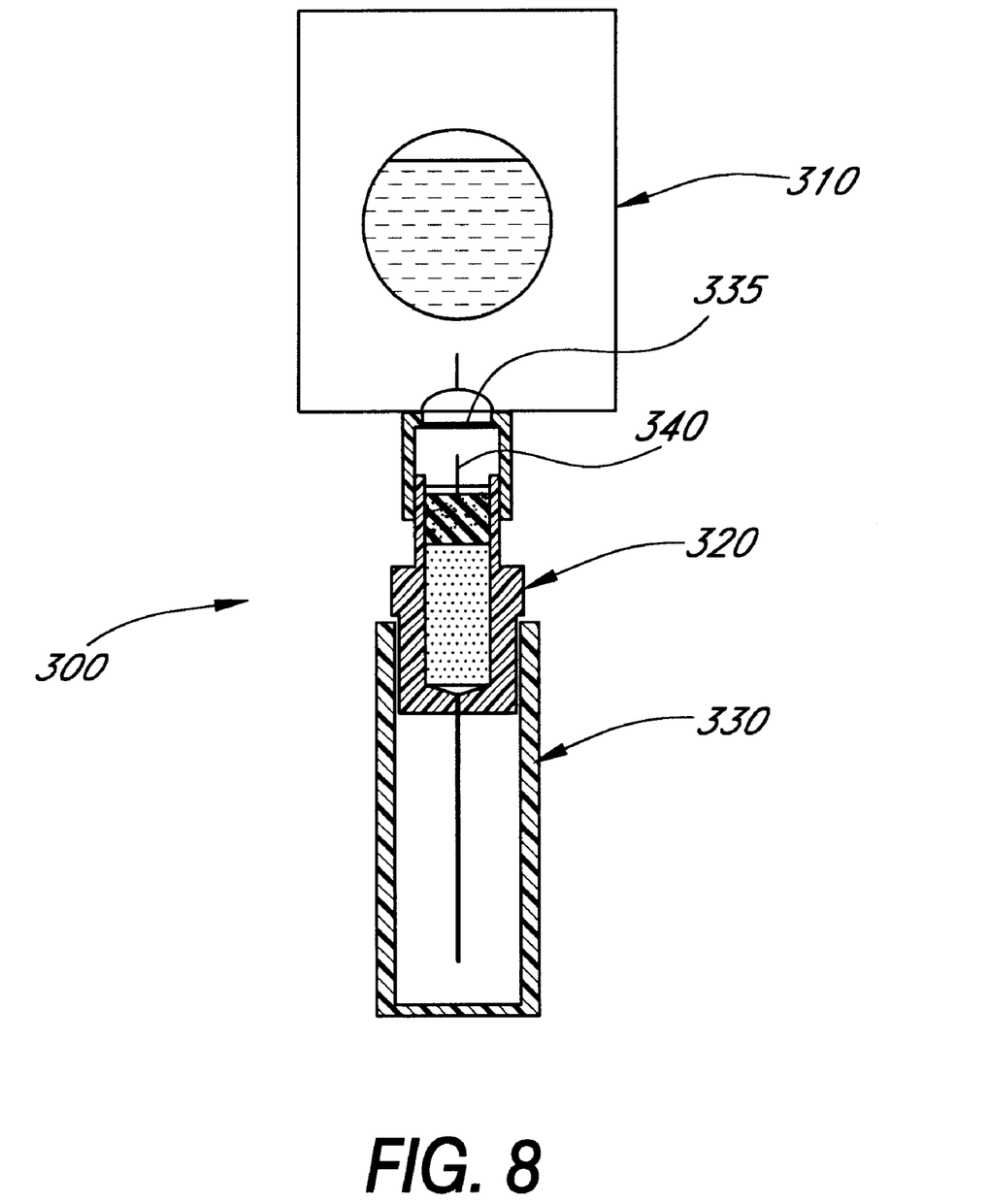
FIG. 8 is a schematic cross-section of a microinjector, constructed in accordance with another embodiment of the invention, incorporating an integral diluent device.

In still another arrangement, illustrated in FIG. 8, a diluent device and microinjector can be integrally provided as an integrated system 300. The illustrated system 300 is similar to that of the two piece system 198 of FIGS. 4–6, including a diluent delivery component 310 and a microinjector 320 connected downstream. A base cover 330 protects the injection needle for safety and sterility.

Desirably, the system 300 includes a base cover 330, as shown in FIG. 8. The device includes a mechanism for separating the liquid diluent, from the dried drug until just prior to administration. The mechanism can be a membrane 335, as illustrated, or any other type of barrier that separates the liquid diluent from the dried reagent. In other arrangements, the barrier can comprise a brittle material that breaks under lateral pressure. In still another arrangement, the barrier can be a valve that is opened by the user.

As shown in FIG. 8, a needle 340 can be used to puncture the membrane 335 that separates the diluent from the dried reagent. In order to administer the drug, the user pushes the needle 340 through the membrane 335 so that the diluent flows into the chamber or compartment that houses the dried drug. As will be appreciated by the skilled artisan, a two-position ratcheting mechanism, allowing the microinjector module 320 to slide upwardly with respect to the diluent delivery module 310, can accomplish the puncturing motion.

Advantageously, the preferred embodiments facilitate rapid preparation of a single dose of deliverable fluid suitable for direct use. Desirably, dissolution or suspension occurs as diluent flows through the unit in a single pass, without circulation or agitation to aid the mixing process. It will be understood, however, that a hydrophobic plug within the terminus 22 and/or the needle constriction preferably ensure complete wetting of the reagent bed 15 during the single-pass flow.

In one embodiment, the fluid is delivered directly (i.e., straight from the microinjector) via an injection needle into a patient. In another embodiment, the fluid is delivered directly into an IV drip line, without gathering in a diffusion or mixing chamber. The latter embodiment can involve injection into an IV line with a needle or needleless connection to the IV line. Alternatively, the dissolved reagent can be employed in any other suitable fashion (e.g., stored). In any case, the preferred embodiments desirably provide single-dose quantities of deliverable fluid from stable, dry, reagents, without the need for any agitation or slow diffusion to aid further dissolution, and without the need for separately measuring the dosage amount after dissolution (or otherwise reconstituting the drug in fluid form). Voids and channels are not formed during the dissolution of the reagents, such that the reagents are quickly and completely dissolved as diluent passes through the system.

Thus, small doses of medically useful compounds are readily converted from stable dry form into deliverable fluid form. Considerable time can be saved in the preparation and delivery of single-dose units, without the risk of storing reagents in unstable fluid forms. Exemplary contexts for which the illustrated devices are particularly useful include delivery of vaccines, particularly in remote locations; emergency administration of chemical weapon antidotes; emergency administration of drugs for the suppression of allergic reactions; scheduled or emergency delivery of supplemental hormones; etc.

Those skilled in the art will readily appreciate that various omissions, additions and modifications may be made to the processes described above without departing from the scope of the invention, and that all such modifications and changes are intended to fall within the scope of the invention, as defined by the appended claims.

I claim:

1. A system for delivering single dose units of medical reagents in fluid form, comprising:

a chamber including a dry reagent bed having a mass of no more than about 1.0 g;

a compression component in the chamber for exerting pressure upon the reagent bed, wherein the compression component comprises an open cell foam; and a delivery mechanism integrally connected and downstream of the chamber for delivering the reagent in a liquid.

2. The system of claim 1, wherein the delivery mechanism comprises a needle.

3. The system of claim 1, wherein the reagent is a drug that has activity in a patient.

4. The system of claim 1, wherein the reagent bed has a mass between about 10 $\mu$g and 500 mg.

5. The system of claim 1, wherein the reagent bed has a mass between about 1 mg to 25 mg.

6. The system of claim 1, further comprising a diluent delivery device configured to connect upstream of the chamber.

7. The system of claim 6, wherein the diluent delivery device comprises a fixed volume of diluent.

8. The system of claim 7, wherein the fixed volume comprises between about 0.1 mL and 10 mL.

9. The system of claim 8, wherein the fixed volume comprises between about 0.1 mL and 1 mL.

10. The system of claim 6, wherein the diluent delivery device is integrally connected to the chamber.

11. The system of claim 6, wherein the diluent delivery device comprises a bioactive ingredient.

12. The system of claim 6, comprising a seal between the chamber and diluent delivery device when connected.

13. The system of claim 12, further comprising a mechanism for selectively opening said seal.

14. The system of claim 13, wherein said mechanism for selectively opening said seal comprises an internal needle selectively communicating fluid between the diluent delivery device and the chamber.

15. A device for delivering small quantities of drugs, comprising:

a chamber defined between a sealed inlet at an upstream end and a outlet at a downstream end;

a dry reagent bed including at least one bioactive ingredient housed within the chamber;

a spring element biased to compact the dry reagent bed housed within the chamber, wherein the spring element comprises an open cell foam; and an injection needle integral with the chamber and in fluid communication with the outlet.

16. The device of claim 15, further comprising a hydrophobic plug between the needle and the reagent bed.

17. The device of claim 16, wherein the spring element is interposed between the dry reagent bed and the sealed inlet.

18. The device of claim 15, wherein the dry reagent bed has a mass between about 1 mg and 100 mg.

19. The device of claim 15, wherein the dry reagent bed has a mass between about 1 mg and 25 mg.

20. A reagent delivery system, comprising:

a first compartment comprising a diluent;

a second compartment providing a dry reagent therein;

a compacting mechanism in the second compartment for exerting pressure upon the dry reagent, wherein the compacting mechanism comprises an open cell foam;

a barrier separating the first compartment from the second compartment;

a first mechanism for selectively delivering the diluent from the first compartment to the second compartment to form a fluid carrying the reagent; and a second mechanism for delivering the fluid carrying the reagent outside the system.

21. The system of claim 20, wherein the diluent has a volume of less than about 100 mL.

22. The system of claim 20, wherein the first mechanism and the second mechanism comprise needles.

23. The system of claim 20, further comprising an adaptor connecting the first compartment to the second compartment.

24. A method of preparing and delivering a defined drug dose, comprising:

converting a dry reagent into a fluid form by flowing a diluent along a laminar flow path through a chamber that houses the dry reagent;

compacting the dry reagent with a compacting mechanism while flowing the diluent through the dry reagent; and delivering the fluid from the chamber directly into a delivery mechanism in fluid communication with a drug recipient.

25. The method of claim 24, wherein the delivery mechanism comprises an injection-needle.

26. The method of claim 24, wherein the delivery mechanism comprises an IV drip line.

27. The method of claim 24, further comprising piercing a seal between an upstream diluent delivery device and the chamber.

28. The method of claim 24, further comprising placing a diluent source housing a fixed fluid volume of less than about 100 mL in fluid communication with the chamber.

29. The method of claim 24, wherein converting comprises dissolving.

30. The method of claim 24, wherein converting comprises suspending.

31. A method of delivering a desired dose of reagent in fluid form, comprising:

providing the desired dose of reagent in dry form;

producing the fluid form by flowing diluent through the reagent in dry form;

compressing the reagent with a compressing mechanism while flowing the diluent through the dry reagent; and delivering the desired dose to a patient without measuring the fluid form.

* * * * *